United States Patent [19]

Townsend et al.

[11] 4,187,241
[45] Feb. 5, 1980

[54] METAL PHOSPHINE COMPLEX

[75] Inventors: John M. Townsend, Montclair; Donald H. Valentine, Jr., Highland Park, both of N.J.

[73] Assignee: Hoffman-La Roche Inc., Nutley, N.J.

[21] Appl. No.: 904,688

[22] Filed: May 10, 1978

Related U.S. Application Data

[62] Division of Ser. No. 816,235, Jul. 18, 1977, Pat. No. 4,120,870.

[51] Int. Cl.$^2$ .............................................. C07F 1/08
[52] U.S. Cl. ................................................. 260/438.1
[58] Field of Search ................. 260/438.1, 430, 429.9, 260/433, 429 R, 432, 431

[56] References Cited

U.S. PATENT DOCUMENTS

| | | | |
|---|---|---|---|
| 3,345,392 | 10/1967 | Graipon et al. | 260/438.1 |
| 3,355,439 | 11/1967 | Welch et al. | 260/438.1 X |
| 3,428,597 | 2/1969 | Dikötter et al. | 260/438.1 X |
| 3,453,299 | 7/1969 | Claridge | 260/438.1 X |
| 3,732,329 | 5/1973 | Thatcher et al. | 260/438.1 X |
| 3,798,241 | 3/1974 | Kagan et al. | 260/340.9 |
| 3,859,092 | 1/1975 | Gipling et al. | 260/438.1 X |
| 3,959,220 | 5/1976 | Hechenbleikner et al. | 260/438.1 X |
| 3,978,101 | 8/1976 | Aviron-Violet | 260/429 R |
| 4,008,281 | 2/1977 | Knowles et al. | 260/429 R |
| 4,119,652 | 10/1978 | Knowles et al. | 260/429 R |
| 4,120,870 | 10/1978 | Townsend | 260/438.1 X |
| 4,124,533 | 11/1978 | Knowles et al. | 260/429 R |

*Primary Examiner*—Helen M. S. Sneed
*Attorney, Agent, or Firm*—Jon S. Saxe; Bernard S. Leon; George W. Johnston

[57] ABSTRACT

Novel Group IB and IIB metal phosphine complexes are disclosed. These complexes are reacted with rhodium complex precursors to form useful enantioselective hydrogenation catalysts. Also disclosed is a method of preparing useful compounds having optical activity such as natural products and compounds useful as flavors and fragrances.

2 Claims, No Drawings

METAL PHOSPHINE COMPLEX

This is a divisional of application Ser. No. 816,235, filed July 18, 1977, now U.S. Pat. No. 4,120,870.

BACKGROUND OF THE INVENTION

Soluble rhodium complexes containing coordinated chiral phosphines catalyze the hydrogenation of prochiral olefins to give optically active alkane derivatives (Knowles et al. U.S. Pat. No. 3,849,840). Particularly useful are hydrogenations of prochiral enamides to form an excess of one enantiomer of a chiral N-acyl amine derivative (Knowles et al. U.S. Pat. Nos. 4,005,127 and 4,008,281; Kagan et al. U.S. Pat. No. 3,798,241; Aviron-Violet U.S. Pat. No. 3,949,000), i.e.,

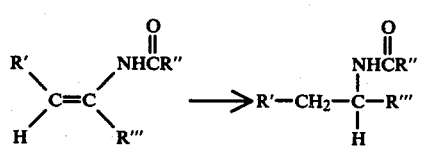

wherein the above R groups may be alkyl, cycloalkyl or aryl, etc. These hydrogenations result in the formation of chiral natural products and substances useful as flavorings and pharmaceuticals.

Asymmetric hydrogenation, per se, has been widely studied as evidenced by the following review articles:

Kagan, *Pure Appl. Chem.*, 43 401 (1975);
Scott et al., *Science*, 184, 943 (1974);
Birch et al., *Organic Reactions*, 24, 1 (1976); and
Marko et al., *Catal. Rev.*, 8, 219 (1973).

Catalysts for these hydrogenations are typically prepared by combining some suitable Group VIIIb metal olefin complex starting material, preferably rhodium, e.g., $\mu,\mu'$-dichloro-bis-(1,5-cyclooctadiene rhodium), with the desired chiral phosphine. Depending on the circumstances, the rhodium phosphine complex thus formed is either isolated or a solution thereof is used directly to catalyze hydrogenations.

The foregoing procedures are generally satisfactory. However, in other instances these procedures are difficult and, at best, inconvenient because of problems encountered in isolation and purification of the phosphine component of the catalyst, e.g., when the phosphine is an oil and/or air-sensitive.

The chiral chelating bis-phosphine (4R,5R)-trans-4,5-bis-(di-3-tolylphosphinomethyl)-2,2-dimethyl-1,3-dioxolane (3-tolyl DIOP) is useful in forming rhodium complex catalysts for enantioselective hydrogenations of enamides (Kagan et al., *J. Organometal Chem.*, 91, 105 [1975]). The utility of this phosphine and similar such substances in like applications is severely limited by the fact that this phosphine is an oil and thus is difficult to isolate contamination-free other than by tedious chromatographic purification techniques.

It is an object of this invention to provide an improved method for the obtention of rhodium complex catalyst compositions containing (4R,5R)-trans-4,5-bis-(di-3-tolylphosphinomethyl)-2,2-dimethyl-1,3-dioxolane and related diphosphines.

DESCRIPTION OF THE INVENTION

In accordance with this invention there are provided novel Group IB and IIB metal complexes of (4R,5R)-trans-4,5-bis-(di-3-tolylphosphinomethyl)-2,2-dimethyl-1,3-dioxolane and related chiral chelating bis-phosphines. These crystalline complexes may be obtained from crude or partially purified chiral chelating bis-phosphines. As described hereinbelow this invention also provides a method of obtaining pure phosphine containing Group IB or IIB metal complexes. These complexes are reacted with suitable rhodium olefin complex precursors to provide soluble catalyst systems for enantioselective hydrogenations of prochiral olefins. These catalysts equal or exceed the enantioselectivity of catalysts formed from the same rhodium complex precursors and highly purified chiral chelating bis-phosphine. The advantage of the catalysts prepared in accordance with this invention is the obviation of the need to employ tedious purification techniques in order to obtain a highly purified chiral chelating bis-phosphine.

The novel metal salt complexes contemplated herein are compounds of the formula:

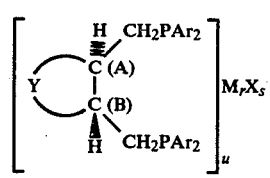

wherein Ar is unsubstituted or substituted aryl; P is phosphorus; M is a Group IB or IIB metal; X is halogen, perchlorate, tetrahalogenoborate, hexahalogenophosphate or hexahalogenoantimonate wherein the said halogenates comprise fluorine and chlorine, and tetraphenylborate; u is an integer from 1-3 and r and s are 1 or 2 depending on the value of u and the valence of M; Y is a group which connects carbons A and B to form an unsubstituted or substituted 4, 5 or 6 membered ring which may contain carbon or both carbon and oxygen atoms.

Although only one enantiomer of compound I is illustrated, the compound is not to be construed as limited thereto. Additionally, the compounds of formula I may exist as dimers and/or oligomers.

Compound I is prepared by reacting a compound of the formula

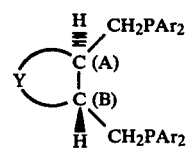

wherein P, Y and Ar are as defined above and a compound of the formula

wherein M, X, r and s are as defined above.

Another aspect of this invention relates to asymmetric hydrogenation. More specifically, the invention relates to homogeneous hydrogenations catalyzed by Group IB and IIB metal salt complexes of chiral tertiary phosphines in combination with Group VIIIb metal olefin complexes wherein the hydrogenation occurs enantioselectively resulting in optically active compounds.

In accordance with this invention compounds having the formula

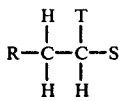

wherein R is alkyl, alkenyl, aryl, substituted or unsubstituted indolyl, with said substituents being selected from the group consisting of lower alkyl and halogen; S is substituted amino; T is lower alkyl, aryl, carboxy, lower alkoxycarbonyl and carboxamido, are prepared by the enantioselective hydrogenation of compounds of the formula

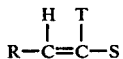

wherein R, S and T are as defined above
where said hydrogenation is conducted in the presence of a Group IB or IIB metal salt complex of a chiral tertiary phosphine and a Group VIIIb metal complex in a solvent medium. The optically active compounds produced by the instant process are obtained as a mixture of enantiomers having an excess of either R- or S-enantiomer. The enantiomer in excess will be dictated by the chiral phosphine used and the isomeric form of the substrate, i.e., E or Z.

The instant invention thus satisfies a long-felt need by providing to the art a new route toward the preparation of optically active compounds, particularly optically active compounds which are natural products and those utilized as flavors and fragrances.

The term "chiral chelating bis-phosphine" as used herein denotes a compound comprised of two achiral phosphorus centers separated by a 4 carbon chain which is chiral.

The term "prochiral" as used herein refers to a carbon atom center having two like substituents, i.e., $CZ_2XY$, such that a change in one of said like substituents leads to a chiral carbon atom center, i.e., CWXYZ.

The term "lower alkyl" refers to an alkyl group having saturated aliphatic straight or branched chains of from 1–6 carbon atoms. Exemplary of the hydrocarbon groups contemplated are methyl, ethyl, propyl, isopropyl, 3-methylbutyl and the like. The term "alkyl" refers to an alkyl group as described above having from 1–20 carbon atoms.

The term "aryl" includes mono-nuclear aryl groups such as phenyl which can be unsubstituted or substituted in one or more positions with a lower alkyl, halogen, an electron denoting group, lower alkoxy, amino, nitro, mono- and di-lower alkylamino, etc., or polynuclear aryl groups such as naphthyl, anthryl, phenanthryl, azulyl, etc., which may be unsubstituted or substituted with one or more of the aforementioned groups.

The term "lower alkenyl" refers to alkenyl groups having unsaturated aliphatic straight or branched chains of from 1–6 carbon atoms. Exemplary of the hydrocarbon groups contemplated are vinyl, propenyl, butenyl, hexenyl, 3-methyl-but-2-enyl and the like. The term "alkenyl" refers to an alkenyl group as described above having from 1–20 carbon atoms.

The term "lower alkanols" refers to alcohols having saturated aliphatic straight or branched chains of 1–7 carbon atoms. Exemplary of the alcohols contemplated are methanol, ethanol, propanol, isopropanol and the like.

The term "lower acyl" refers to acyl groups having 1–6 carbon atoms such as formyl, acetyl, butyryl and the like.

The terms "halo", "halogen," or "halide" encompass chlorine, fluorine, bromine and iodine.

The term "acylamido" refers to amido groups containing 1–6 carbon atoms such as formamido, acetamido, propionamido and the like.

The term "lower alkoxycarbonyl" refers to carbonyl groups having attached thereto lower alkoxy moieties as defined hereinabove.

The term "enantiomeric excess" as used herein refers to a numerical value, expressed in percent, indicating the predominance of one enantiomer in relation to another, e.g., excess of the R-enantiomer expressed as percent of R-enantiomer minus percent of S-enantiomer.

The terms "R- and S-enantiomer" refer to the configuration of the substituents about the asymmetric carbon atom in optically active organic compounds as prescribed in standard IUPAC nomenclature.

The terms "entgegen" (E) and "zusammen" (Z) refer to the disposition of substituents about carbon to carbon double bonds as prescribed in standard IUPAC nomenclature.

In schematic representations of molecular structures, the wedges ( ▲ ) indicate that the substituent is above the plane of the molecule, the broken lines (-----) indicate that the substituents are below the plane of the molecule, and the wavy lines (∽) indicate that the substituents may be either above or below the plane of the molecule.

In accordance with the instant invention, the substrates for hydrogenation include compounds of formula IV having alkyl, alkenyl, aryl, indolyl (or substituted indolyl) substituents. The substituents on the indolyl moiety may be the same as those set forth hereinabove for aryl. Typical compounds falling within the scope of the contemplated substrates include but are not limited to:

α-N-acetylamino acrylic acid;
α-N-acetylaminocinnamic acid;
methyl α-N-acetylaminocinnamate;
α-N-benzoylamino-(3-methoxy-4-hydroxyphenyl)-3-acrylic acid;
α-N-acetylamino-(3-methoxy-4-acetoxyphenyl)-3-acrylic acid;
Z-α-N-acetylamino-6-methylindole-3-acrylic acid;
ethyl Z-α-N-acetylamino-(6-methylindole)-3-acrylate;
α-N-acetylamino-(4-hydroxyphenyl)-3-acrylic acid;
α-N-acetylamino-(3,4-methylenedioxy)-3-acrylic acid; and
α-N-acetylaminocinnanamide.

The process described herein may be applied to E- or Z- isomers of the compounds of formula II or mixtures thereof. To obtain products containing a higher enantiomeric excess, however, it is usually preferred to use a pure isomer or mixtures containing a predominance of one isomer. Use of the Z-isomer is particularly preferred.

The hydrogenation catalyst utilized herein is the soluble reaction product obtained by combining a novel metal complex of formula I with a Group VIIIb metal salt or metal complex. The Group VIIIb metals include rhodium, ruthenium, nickel, palladium, platinum or iridium. The rhodium metal salts or metal complexes are particularly preferred.

An overall procedure for the preparation of compound I is as follows:

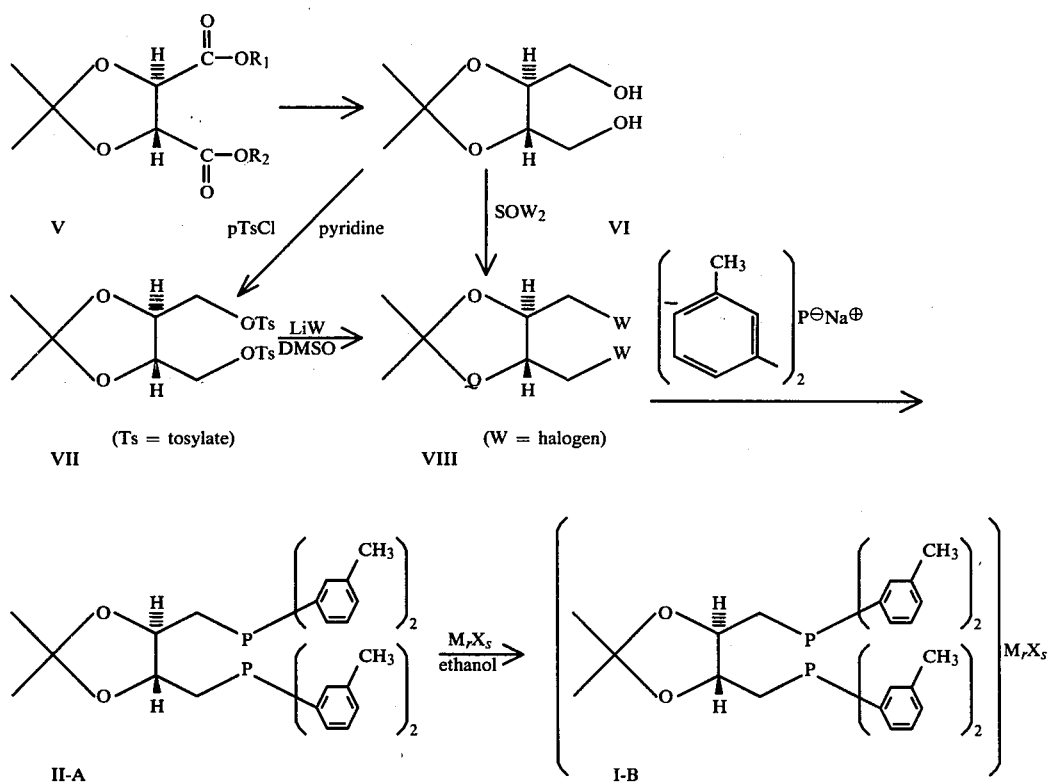

Suitable rhodium salts or complexes include RhCl$_3$·nH$_2$O, Rh(acetylacetonate)$_3$, [RhZ(olefin)$_2$]$_2$ and [RhZ(diolefin)]$_2$ where Z is halogen, lower alkoxycarbonyl and lower alkyl derivatives of acetylacetone, preferably acetylacetone itself. The term "olefin" as used herein means an olefinic compound such as ethylene or propylene and the term "diolefin" as used herein means a diolefinic compound such as 1,5-hexadiene, 1,5-cyclooctadiene, norbornadiene and the like. Preferred rhodium salts or complexes include $\mu,\mu'$-dichloro-bis-[bis(olefin)rhodium(I)], e.g., $\mu,\mu'$-dichloro-bis-[1,5-cyclooctadiene rhodium(I)] or $\mu,\mu'$-dichloro-bis-[bis-(ethylene)rhodium(I)].

Preferably the chiral tertiary copper containing phosphines utilizes in the instant invention are the reaction product of a compound of the formula

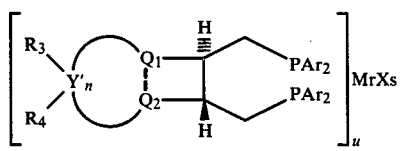

wherein R$_3$ and R$_4$ are alkyl or aryl; Y' is carbon; Q$_1$ and Q$_2$ are methylene or oxygen; P, Ar, M, X, u, r and s are as defined above; n is an integer from 0–1, with the proviso that when n=0, Q$_1$ and Q$_2$ are methylene and the dotted line is a carbon-carbon bond and when n=1, Y' is carbon and Q$_1$ and Q$_2$ are oxygen where each oxygen is bonded to Y', the dimers and oligomers thereof, and a complex of a metal selected from those mentioned hereinabove.

A preferred starting material is the tosylate of compound VII. The ditosylate in the above scheme, which can be prepared by known methods, is treated with a halogenating agent to form the corresponding halide. The resulting halide is then treated with an alkali metal diarylphosphide, preferably di-m-tolylphosphide, to form the crude chiral chelating bis-phosphine. The chelating bis-phosphine is then treated with a Group IB or IIB metal salt to form the compound of formula I.

The halogenation of the ditosylate may be accomplished by treating said ditosylate with alkali metal halides. This reaction is generally conducted in a polar solvent such as dimethylsulfoxide (DMSO), dimethylformamide (DMF) or acetone.

The resulting dihalide is then treated with an alkali metal diarylphosphide, such as di-m-tolylphosphide, to form the resulting chiral chelating bis-diarylphosphine of formula II. This reaction is generally carried out in a solvent, preferably liquid ammonia or an ethereal solvent such as diethyl ether or tetrahydrofuran. This reaction is generally carried out at a temperature of from −33° C. to +50° C.

The resulting chiral chelating bis-phosphine II is then reacted with a Group IB or IIB metal salt, preferably cuprous chloride, in a lower alkanol solvent, preferably ethanol. Although temperature and pressure are not critical, the reaction is generally carried out at atmospheric pressure and at the reflux temperature of the solvent.

Rather than employing the ditosylate as the starting material, there may be employed the alcohol precursor thereof, a compound of the formula

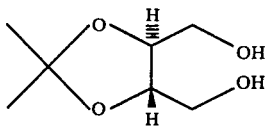

VI which may be converted directly to the dihalide by treatment with conventional halogenating agents such as thionyl chloride, phosphorus trihalide and phosphorus pentahalide. The dihalide may then be further reacted as described hereinabove to form compound I.

Compound VI may be prepared from the methyl or ethyl ester of tartaric acid. The methyl or ethyl ester of tartaric acid is prepared in a conventional manner. The aforementioned esters are then transformed to a compound of the formula

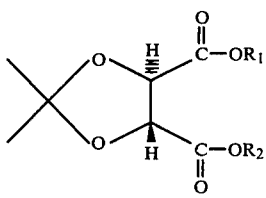

V wherein $R_1$ and $R_2$ are methyl or ethyl
by treating said esters with acetone dimethyl or diethyl acetal.

Compound VI is then prepared by reduction of compound V. The reducing agents which may be employed to accomplish the transformation of compound V to compound VI include $LiAlH_4$, $NaBH_4$ and Vitride ® (a registered trademark of Alpha Chemical Co. for $NaAlH_2[OCH_2CH_2-O-CH_3]_2$). $NaBH_4$ is the reducing agent of choice where $R_1$ and $R_2$ of formula V are ethyl. Preferred reducing agents are $LiAlH_4$ and $NaBH_4$. The alcohol of compound VI then obtained may be further reacted to form compound I as described hereinabove.

The compound of formula I is then reacted with one of the Group VIIIb metal complexes, preferably rhodium complexes, mentioned hereinabove to form the novel asymmetric hydrogenation catalyst of this invention. This hydrogenation catalyst is generally formed in situ and not isolated, although it may be isolated and stored for later use, if desired.

The molar ratio of the compound of formula I to the Group VIIIb metal salt source which is reacted to form the complex catalysts used herein is generally adjusted so that the optimum of P/Group VIIIb metal is obtained. In the case of rhodium, this preferred ratio is 2:1 (i.e., one mole of chiral chelating diphosphine per g-atom of rhodium. Ratios generally of 2:1 to 10:1 may be used. Higher ratios may be utilized but no particular benefits are gained thereby. In the case of Group VIIIb metals other than rhodium, the P/Group VIIIb metal may vary from 1:1 to about 10:1, the optimum being determinable by those skilled in the art.

The molar ratio of the substrate of formula IV to catalyst may preferably vary from about 1:1 to about 5000:1, although ratios greater than 5000:1 may also be used.

The preferred solvents employed in the asymmetric hydrogenation process disclosed herein may be selected from lower alkanols alone or lower alkanols in combination with aromatic hydrocarbons or saturated alkanes or cycloalkanes or lower alkanols in combination with water. The lower alkanols are as previously defined. The term "aromatic hydrocarbons" refers to benzene, toluene, xylene and the like, although any inert aromatic hydrocarbon may be used. The term "saturated alkanes or cycloalkanes" refers to pentane, hexane, heptane, cyclohexane and the like, although any inert saturated alkane or cycloalkane containing 5-20 carbons may be used.

In carrying out the instant hydrogenation, temperature and pressure are not critical. The temperature may range from about $-30°$ C. to about $150°$ C., preferably from about $0°$ C. to about $50°$ C. The pressure may range from about 2 psi to about 500 psi, preferably about 2-100 psi.

The process of the instant invention is particularly adaptable to the formation of tryptophans of the formula

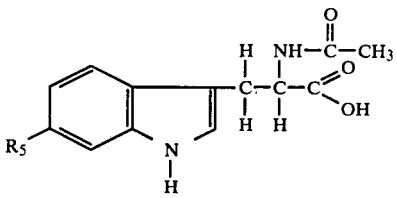

wherein $R_5$ is lower alkyl or halogen
which are useful as non-nutritive sweeteners. The above tryptophan is obtained by the asymmetric hydrogenation of a compound of the formula

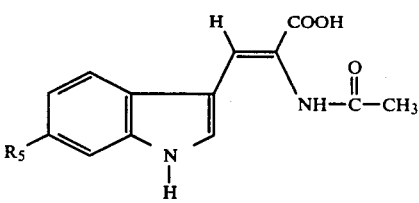

wherein $R_5$ is as above.

The preparation of the above tryptophan by the asymmetric hydrogenation process of this invention constitutes an improvement over the asymmetric hydrogenation techniques employed in application Ser. No. 698,573 to Batcho et al. filed June 22, 1976, the disclosure of which is incorporated herein by reference. The instant process may also be employed to asymmetrically hydrogenate the substrates disclosed in Batcho et al.

The novel asymmetric catalyst components of formula I are particularly advantageous in that they are solids which are soluble in the reaction solvents employed in the hydrogenation step. Furthermore, the fact that these catalyst components are solid makes the handling and storage thereof immensely simple as compared to prior art asymmetric hydrogenation catalysts having chiral phosphine components which are generally oily liquids. An additional advantage is that purification of the phosphine, prior to reacting same with the compound of formula $M_rX_s$ is not necessary. This advantage is singularly striking in that the prior art asymmetric catalysts require purification of the chiral phosphine component, usually accomplished by chromatographic techniques, before utilization in hydrogenation.

The utility of these novel Group IB and IIB metal containing chiral phosphines is not limited to hydrogenations. These catalyst components may be employed to prepare catalysts to effect other reactions such as enantioselective hydrosilylations, hydroformylations and hydroesterifications when combined with suitable Group VIIIb metal complexes.

The following non-limiting examples illustrate the process of the instant invention. All ratios are by weight unless otherwise stated. The wedges and broken lines have the significance previously described.

The enantiomeric excess was calculated in accordance with the following equation:

enantiomeric excess of R-enantiomer (in percent) =
$$100 \left(1 - \frac{2}{\left(1 + \frac{R}{S}\right)}\right)$$

wherein the parameter (R/S) was determined by a quantitative, liquid chromatographic analysis of diastereomeric dipeptide derivatives of the amino acid obtained from the hydrogenation product by hydrolysis.

In the examples the term "DIOP" refers to (−)-4R,5R-trans-4,5-bis-(diphenylphosphinomethyl)-2,2-dimethyl-1,3-dioxolane. Similarly, the term "(3-CH$_3$)DIOP" refers to (−)-4R,5R-trans-4,5-bis-(di-(m-tolyl)phosphinomethyl)-2,2-dimethyl-1,3-dioxolane and the term "(3,5-diCH$_3$)DIOP" refers to (+)-4R,5R-trans-4,5-bis-([di-3,5-dimethylphenyl]phosphinomethyl)-2,2-dimethyl-1,3-dioxolane.

EXAMPLE 1

Partially purified (−)-4R,5R-trans-4,5-bis-(di-(m-tolyl)phosphinomethyl)-2,2-dimethyl-1,3-dioxolane ("(3-CH$_3$)DIOP") was obtained from a column chromatography of a crude product produced by combining sodium di-(m-tolyl)phosphide with ditosylate 1. This chromatography employed 130 g. silica gel/g. crude phosphine.

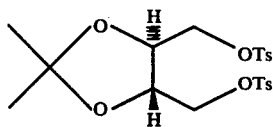

Approximately 600 mg. of this partially purified (3-CH$_3$)DIOP was combined with 100 mg. of cuprous chloride and 10 ml. of absolute ethanol. After 5 minutes of reflux over the steam bath, the warm solution was decanted from traces of unreacted cuprous chloride. Upon cooling, the product precipitated and there was collected 530 mg. of colorless solid. Recrystallization from 8 ml. of boiling absolute ethanol provided 500 mg. (ca. 66%) of colorless crystals of (3-CH$_3$)DIOP-CuCl complex, m.p. 108° (dec.), $[\alpha]_D^{25}$+94.3° (3.0% benzene).

Anal Calcd. for C$_{35}$H$_{40}$ClCuO$_2$P$_2$.C$_2$H$_5$OH: C, 63.50; H, 6.63; P, 9.16; Cu, 9.38; Cl, 5.19; Found: C, 63.51; H, 6.48; P, 8.85; Cu, 9.38; Cl, 5.06.

EXAMPLE 2

2.8 g. of crude (3-CH$_3$)DIOP (purity estimated to be 70–80% by tlc) obtained by combining lithium di(m-tolyl)phosphide [obtained from di(m-tolyl)phosphine and n-BuLi] with dichloride 2,

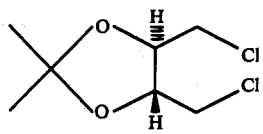

was dissolved in 43 ml. of deoxygenated absolute ethanol and treated with 0.5 g. of cuprous chloride. The mixture was refluxed over a steam bath for five minutes, filtered hot, and cooled to room temperature and finally to 0°. A small quantity of gummy solid was removed by filtration and then the filtrate was concentrated to 10 ml. and again cooled to 0°. After 2 days at 0°, filtration provided 1.6 g. (ca 54% based on 2) of off-white solid complex, m.p. 86°–92° (dec.). This crude (3-CH$_3$)DIOP-CuCl complex was used directly for catalytic hydrogenations, as in Example 10.

EXAMPLE 3

(−)-1R,2R-trans-1,2-Bis-(diphenylphosphinomethyl)cyclobutane and cuprous chloride were combined with absolute ethanol and heated over the steam bath for 5–10 minutes as in Example 1. The crystalline complex was obtained upon cooling, m.p. 197°–199.5°, $[\alpha]_D^{25}$+67.6° (1.0%, chloroform).

Anal. Calcd. for C$_{30}$H$_{30}$ClCuP$_2$: C, 65.34; H, 5.48; Cu, 11.52; Cl, 6.43; P, 11.23; Found: C, 65.48; H, 5.27; Cu, 11.53; Cl, 6.34; P, 11.52.

EXAMPLE 4

(+)-4R,5R-trans-4,5-Bis([di-3,5-dimethylphenyl]phosphinomethyl)-2,2-dimethyl-1,3-dioxolane ("(3,5-diCH$_3$)DIOP"), and cuprous chloride were combined with absolute ethanol and refluxed for 5 minutes. The solution was filtered hot to remove traces of unreacted cuprous chloride and cooled. The complex which crystallized upon cooling contained approximately 0.67 mol of ethanol; 62% yield, m.p. 129°–131°, $[\alpha]_D^{25}$ 42.5° (1.0%, chloroform).

Anal. Calcd. for C$_{39}$H$_{48}$ClCuO$_2$P$_2$.0.67CH$_3$CH$_2$OH: C, 65.42; H, 7.08; Cl, 4.79; P, 8/36; Found: C, 65.31; H, 7.32; Cl, 4.76; P, 9.44.

EXAMPLE 5

(−)-4R,5R-trans-4,5-Bis(diphenylphosphinomethyl)-2,2-dimethyl-1,3-dioxolane, ("DIOP"), and cuprous chloride were refluxed in absolute ethanol for five minutes, filtered and cooled to room temperature. When no complex precipitated, the ethanol was removed at reduced pressure and the residue was crystallized from cyclohexane. There was obtained colorless crystals, m.p. 116°–118° of "lower-melting" DIOP-CuCl complex, used in hydrogenation as in Example 13. The microanalysis of this material suggested the formulation (CuCl)$_2$(DIOP)$_3$.1.5 cyclohexane.

Anal. Calcd. for C$_{93}$H$_{96}$Cu$_2$Cl$_2$O$_6$P$_6$.C$_9$H$_{18}$: C, 67.31; H, 6.31; Cl, 3.90; P, 10.21; Found: C, 67.28; H, 6.46; Cl, 3.75.

EXAMPLE 6

As in Example 5, DIOP and cuprous chloride were refluxed in absolute ethanol, but in this case, the mixture was refluxed for fifteen minutes until crystals of the product began to separate from the hot solution. The solid obtained by filtration was dissolved in chloroform and filtered again to remove traces of unreacted cuprous chloride. The chloroform was removed and the remaining powder was crystallized twice from 1:1 benzene-methanol to give the pure "high-melting" DIOP-CuCl complex, m.p. 211°–212°, $[\alpha]_D^{25}$ 36.5° (1.0%, chloroform).

Anal. Calcd. for $C_{31}H_{32}ClCuO_2P_2$: C, 62.31; H, 5.40; Cl, 5.93; P, 10.37; Cu, 10.63; Found: C, 62.30; H, 5.38; Cl, 5.69; P, 10.69; Cu, 10.90.

EXAMPLE 7

Equivalent amounts of (3-CH₃)-DIOP and silver perchloride were combined and refluxed in absolute ethanol. The product began to separate within seconds. After five minutes, the mixture was cooled and filtered to give analytically pure (3-CH₃)-DIOP-AgClO₄ complex, m.p. 231°–233° (dec.), $[\alpha]_D^{25}$ −30.4° (1.0%, chloroform).

Anal. Calcd. for $C_{35}H_{40}AgClO_6P_2$: C, 55.17; H, 5.29; Cl, 4.65; P, 8.13; Found: C, 55.05; H, 5.24; Cl, 4.91; P, 8.32.

EXAMPLE 8

Zinc perchlorate and (3-CH₃)-DIOP (10% excess) were refluxed under argon in deoxygenated absolute ethanol for 18 hours. After cooling, the solution was evaporated to dryness and the residue was triturated successively with ether, benzene, water and ether-petroleum ether. The colorless residue had apparently undergone slight hydrolysis according to the microanalysis and to the presence of a moderate —OH stretching absorption in its infrared spectrum. The material was used as is in a catalytic hydrogenation, as in Example 16.

Anal. Calcd. for $C_{35}H_{40}Cl_2O_{10}P_2Zn$: C, 51.33; H, 4.92; Cl, 8.66; Found: C, 52.18; H, 5.18; Cl, 8.58.

EXAMPLE 9

A slurry of 2.0 g. of Z-α-N-acetylamino-6-methylindole-3-acrylic acid and 8.5 ml. of deoxygenated methanol was treated under anaerobic conditions with 1.49 ml. of a catalyst solution prepared from $14.7 \times 10^{-3}$ g. of (3-CH₃)-DIOP-CuCl-ethanolate complex prepared as in Example 1, $5.2 \times 10^{-3}$ g. of μ,μ'-dichloro-bis-[1,5-cyclooctadienerhodium (I)] and 25 ml. of methanol. This catalyst solution contains $0.78 \times 10^{-3}$ g. catalyst per ml. of solution; thus use of 1.49 ml. corresponds to a substrate/catalyst weight ratio of 1720/1. The reaction mixture was placed in a pressure vessel and stirred under an initial hydrogen pressure of 40 psig at 23° C. After 1 hour 50 minutes, approximately 86% of the ultimate pressure drop had occurred and the mixture became homogeneous. After 14 hours, no further pressure change was observed. Solvent removal left 2.0 g. (100%) of R-(−)-N-acetyl-6-methyltryptophan having $[\alpha]_D^{25}$ −22.09° (c 1.0%, CH₃OH). The R/S enantiomer ratio was determined for the crude amino acid obtained by hydrolysis of the hydrogenation product. There was found to be present an 84.4% enantiomeric excess (e.e.) of the R enantiomer, i.e., 92.2 parts R enantiomer and 7.8 parts S enantiomer, according to a quantitative analytical separation of diastereomeric dipeptide derivatives of the amino acid.

EXAMPLE 10

As in Example 9, 2.0 g. of Z-α-N-acetylamino-6-methylindole-3-acrylic acid was combined in a pressure vessel with 9.0 ml. of methanol and a total of 2.4 ml. of catalyst solution prepared from $20.5 \times 10^{-3}$ g. of CuCl-(3-CH₃)-DIOP complex prepared as in Example 2, $7.0 \times 10^{-3}$ g. of μ,μ'-dichloro-bis-[1,5-cyclooctadienerhodium (I)] and 25 ml. of methanol. The substrate to catalyst weight ratio was thus 755/1. The catalyst solution was added in three portions over the course of the hydrogenation. When the pressure change ceased, the solvent was removed to give R-(−)-N-acetyl-6-methyltryptophan, $[\alpha]_D^{25}$ −21.3°. The product had an 82% e.e. of the R enantiomer according to amino acid analysis.

EXAMPLE 11

A hydrogenation reaction was performed as in Examples 9 and 10 except that the catalyst consisted of 3.1 ml. of a solution prepared from $2.5 \times 10^{-3}$ g. of (−)-1R,2R-trans-1,2-bis(diphenylphosphinomethyl)cyclobutane-cuprous chloride complex, $1.1 \times 10^{-3}$ g. of μ,μ'-dichloro-bis-[1,5-cyclooctadienerhodium(I)] and 10 ml. of methanol. This corresponds to a substrate/catalyst weight ratio of 1790/1. The R-(−)-N-acetyl-6-methyltryptophan obtained after hydrogenation as in Example 9 had $[\alpha]_D^{25}$ −17.57°, 60.4% e.e. of R enantiomer by amino acid analysis.

EXAMPLE 12

A hydrogenation was performed as in Examples 9–11 using as catalyst 2.3 ml. of a solution prepared from $8.1 \times 10^{-3}$ g. of CuCl-(3,5-di-CH₃)-DIOP complex, $2.8 \times 10^{-3}$ g. of μ,μ'-dichloro-bis-[1,5-cyclooctadienerhodium (I)] and 25 ml. of methanol. This gives a substrate/catalyst weight ratio of 2000/1. The product R-(−)-N-acetyl-6-methyltryptophan resulting from hydrogenation as in Example 9 had $[\alpha]_D^{25}$ −22.88°, 87% e.e. of the R enantiomer by amino acid analysis.

EXAMPLE 13

A hydrogenation was performed as in Examples 9–12 using as catalyst 1.14 ml. of a solution prepared from $17.2 \times 10^{-3}$ g. of CuCl-DIOP complex prepared as in Example 5, $6.4 \times 10^{-3}$ g. of μ,μ'-dichloro-bis-[1,5-cyclooctadienerhodium (I)] and 25 ml. of methanol. This gives a substrate/catalyst weight ratio of ca. 2000/1. The product R-(−)-N-acetyl-6-methyltryptophan resulting from hydrogenation as in Example 9 had $[\alpha]_D^{25}$ −20.86°, 73% e.e. of the R enantiomer by amino acid analysis.

EXAMPLE 14

A hydrogenation was performed as in Example 9 using as catalyst 1.0 ml. of a solution prepared from $7.6 \times 10^{-3}$ g. of DIOP-CuCl complex prepared as in Example 6, $3.1 \times 10^{-3}$ g. of μ,μ'-dichloro-bis-[1,5-cyclooctadienerhodium (I)] and 10 ml. of methanol. This gives a substrate/catalyst weight ratio of ca. 2000/1. The product R-(−)-N-acetyl-6-methyltryptophan resulting from hydrogenation as in Example 9 had $[\alpha]_D^{25}$ −19.8°, 75.4% e.e. of the R enantiomer by amino acid analysis.

EXAMPLE 15

A hydrogenation was performed as in Example 9 using as catalyst 2.35 ml. of a turbid solution freshly prepared from $12.4 \times 10^{-3}$ g. of AgClO₄-(3-CH₃)-DIOP complex prepared as described in Example 7, $4.6 \times 10^{-3}$ g. of μ,μ'-dichloro-bis-[1,5-cyclooctadienerhodium (I)] and 10 ml. of methanol. This gives a substrate to catalyst weight ratio of 500/1. The product R-(−)-N-acetyl-6-methyltryptophan resulting from hydrogenation as in Example 9 had $[\alpha]_D^{25} -22.87°$, 81.4% e.e. of the R enantiomer by amino acid analysis.

EXAMPLE 16

A hydrogenation was performed as in Example 9 using as catalyst 1.8 ml. of a solution prepared from $16.9 \times 10^{-3}$ g. of solid complex prepared from $Zn(ClO_4)_2$ and (3-CH₃)-DIOP as described in Example 8, $5.1 \times 10^{-3}$ g. of $\mu,\mu'$-dichloro-bis-[1,5-cyclooctadienerhodium (I)] and 10 ml. of methanol. This gives a substrate to catalyst weight ratio of ca. 500/1. The product R-(−)-N-acetyl-6-methyltryptophan resulting from hydrogenation as in Example 9 has $[\alpha]_D^{25}$ −22.92°, 81.6% e.e. of the R enantiomer by amino acid analysis.

We claim:

1. A compound of the formula:

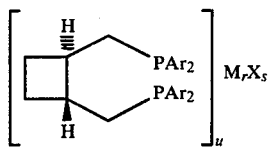

wherein P is phosphorus; Ar is substituted or unsubstituted aryl; M is a Group IB or IIB metal; X is tetraphenylborate, halide, perchlorate, tetrahalogenoborate, hexahalogenophosphate or hexahalogenoantimonate, wherein said halogenates are fluorine or chlorine; u is an integer from 1–3; r and s are 1 or 2 depending on the valence of M and the value of u, the dimers and oligomers thereof.

2. The compound of claim 1 wherein said compound is

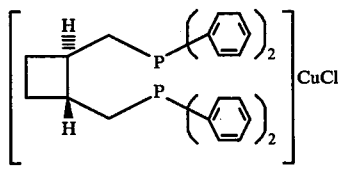

* * * * *